(12) United States Patent
Ciok et al.

(10) Patent No.: US 8,740,867 B2
(45) Date of Patent: Jun. 3, 2014

(54) OSTOMY APPLIANCE

(75) Inventors: Danuta Ciok, Nivaa (DK); Esben Stroebech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 392 days.

(21) Appl. No.: 10/551,282

(22) PCT Filed: Mar. 26, 2004

(86) PCT No.: PCT/DK2004/000211
§ 371 (c)(1),
(2), (4) Date: Aug. 21, 2006

(87) PCT Pub. No.: WO2004/084777
PCT Pub. Date: Oct. 7, 2004

(65) Prior Publication Data
US 2007/0005033 A1     Jan. 4, 2007

(30) Foreign Application Priority Data
Mar. 27, 2003   (DK) ................................ 2003 00471

(51) Int. Cl.
*A61F 5/44* (2006.01)
(52) U.S. Cl.
USPC ............ 604/344; 604/339; 604/342; 604/327
(58) Field of Classification Search
USPC ................................................ 604/332–344
See application file for complete search history.

(56) References Cited

U.S. PATENT DOCUMENTS

| | | |
|---|---|---|
| 3,100,488 A | 8/1963 | Orowan |
| 3,908,658 A * | 9/1975 | Marsan .......................... 604/336 |
| 4,367,732 A | 1/1983 | Poulsen et al. |
| 4,681,574 A | 7/1987 | Eastman |
| 5,051,259 A | 9/1991 | Olsen et al. |
| 5,429,626 A | 7/1995 | Fenton |
| 5,591,144 A * | 1/1997 | Smith et al. .................... 604/327 |
| 5,702,356 A * | 12/1997 | Hathman ......................... 602/41 |
| 5,714,225 A | 2/1998 | Hansen et al. |
| 6,171,594 B1 | 1/2001 | Nielsen |
| 6,303,700 B1 | 10/2001 | Chen |
| 6,332,879 B1 | 12/2001 | Nielsen et al. |
| 6,437,038 B1 | 8/2002 | Chen |
| 6,451,883 B1 | 9/2002 | Chen et al. |

(Continued)

FOREIGN PATENT DOCUMENTS

| | | | |
|---|---|---|---|
| EP | 0 259 184 | 3/1988 | |
| EP | 1 181 910 A1 * | 2/2002 | ............. A61F 5/445 |

(Continued)

*Primary Examiner* — Michele Kidwell
(74) *Attorney, Agent, or Firm* — Coloplast Corp., Coloplast A/S; Nick Baumann

(57) ABSTRACT

An ostomy appliance comprising a front wall and a rear wall of flexible material forming a bag, said rear wall having an opening for receiving a stoma, and said rear wall also being provided with an adhesive wafer for securing the appliance to a user's skin, said wafer having a hole being aligned with the opening for receiving the stoma, wherein the opening has an edge being secured to the surface of the adhesive wafer facing away from the user in an attachment zone surrounding the hole of the wafer, wherein a first part of the edge of the opening of the gab is secured to the surface of the wafer in a corresponding first part of the attachment zone, and wherein a second, remaining part of the edge of the opening of the bag is prepared for adhesive sealing of the same to the remaining second part of the attachment zone renders it possible for a nurse to observe the stoma area during adaptation of such a sealing member when applying one-piece appliances.

9 Claims, 4 Drawing Sheets

(56) References Cited

U.S. PATENT DOCUMENTS

| | | | |
|---|---|---|---|
| 6,509,391 B2 | 1/2003 | Gothjaelpsen et al. | |
| 6,652,496 B2 * | 11/2003 | Bateman | 604/342 |
| 2001/0020156 A1 * | 9/2001 | Whiteside | 604/342 |
| 2007/0255240 A1 * | 11/2007 | Ciok | 604/339 |

FOREIGN PATENT DOCUMENTS

| | | |
|---|---|---|
| EP | 1 254 647 A1 | 11/2002 |
| FR | 2 816 202 | 5/2002 |
| GB | 2 017 501 A | 10/1979 |
| GB | 2 115 291 A | 9/1983 |
| JP | 2001-231802 | 8/2001 |
| WO | WO 98/17212 | 4/1998 |
| WO | WO 98/38952 | 9/1998 |
| WO | WO 98/53771 | 12/1998 |
| WO | WO 99/26565 | 6/1999 |
| WO | WO 00/54820 | 9/2000 |
| WO | WO 01/05340 A2 | 1/2001 |

* cited by examiner

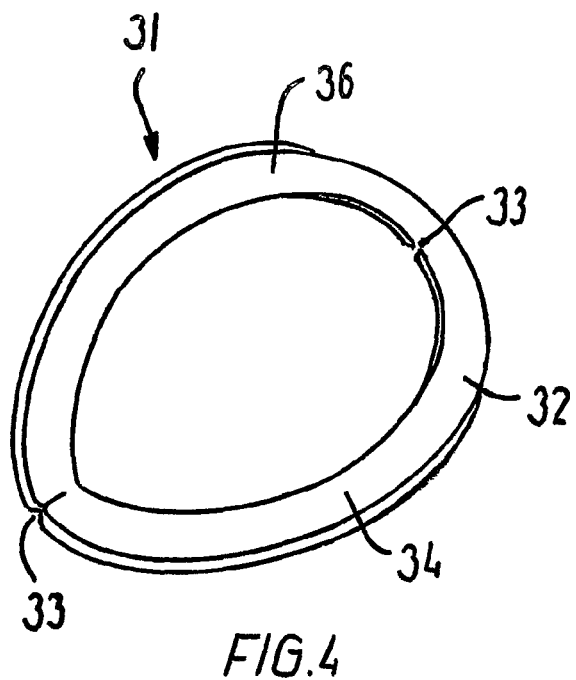
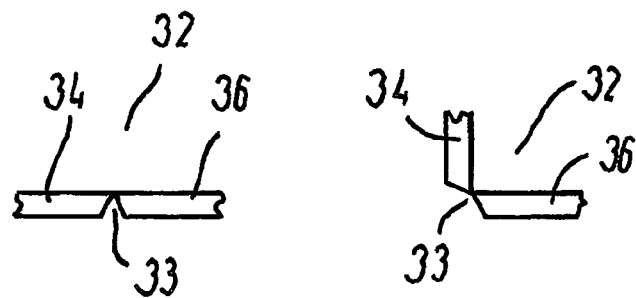
FIG.4
FIG.5a        FIG.5b

OSTOMY APPLIANCE

This is a nationalization of PCT/DK04/000211 filed Mar. 26, 2004 and published in English.

BACKGROUND OF THE INVENTION

1. Field of the Invention

The present invention relates to an ostomy appliance and to a method of applying an ostomy appliance body side member around a stoma.

In connection with surgery for a number of diseases in the gastrointestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is permanently attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may e.g. be a system known per se comprising matching coupling rings or matching flanges and adhesive surfaces engaging with and sealing against a flange area of the body side member.

It is necessary to change the body side member of a two-piece appliance when the centre part of the adhesive wafer has been sufficiently deteriorated to allow access of the aggressive exudates to the skin surrounding the stoma, irrespective of the fact that the wafer as such has a much longer wearing time. The access of aggressive exudates to the skin is causing skin problems.

Frequent changing of the body side member of a two-piece appliance is undesirable due to the irritation of the skin and the quality of life of the user may be improved and the nuisance of the wearing of an ostomy appliance reduced if the intervals between exchanging of body side member can be increased.

The service time of the body side ostomy member depends inter alia of the amount and the aggressiveness of the exudates and of the sealing between the stoma and the body side ostomy member.

The sealing depends on the fit to the stoma. Conventionally, only a limited number of standard appliances having holes of different size are available and the user or an assistant must customise the body side member by cutting the edge of the hole to adapt the body side member to the stoma.

2. Description of the Related Art

When cutting the edge of the hole of an adhesive wafer of a conventional one-piece ostomy appliance for adapting the same to the size and shape of a stoma the cutting is complicated by the fact that in order to secure discretion, for decorative purposes and for providing softness, low noise generation and comfort the bag is often made from an opaque material or covered and/or provided with a cover or front layer rendering it very difficult, if not impossible for the user or the nurse to observe the stoma area during determination of a cutting line for adaptation of the hole or when applying the appliance.

Published International Patent Applications Nos. WO 98/17212 and WO 98/53771 disclose ostomy appliances comprising a body side member comprising an adhesive wafer for securing the appliance to the user's skin, said wafer having a hole for receiving a stoma, and an optionally separately exchangeable receiving member or bag secured to the body side ostomy member for receiving secretions from the ostomy said ostomy appliance further comprising a sealing member disposed in the hole of the wafer surrounding the stoma and having a hole for accommodating the stoma.

The ostomy appliance disclosed in Published International Patent Application No. WO 98/53771 has a sealing member having balanced plastic and elastic properties allowing a better adaptation of the hole of the ostomy appliance to a stoma by a temporary enlarging of the hole by everting or rolling up the inner rim of the hole for accommodating the stoma.

WO 98/17212 and WO 98/53771 only teach the use of such a sealing member together with two-piece ostomy appliances and do neither disclose nor indicate how to use a sealing member together with one-piece ostomy devices.

It has been found desirable in practice to make use of separate sealing members for facilitating the adaptation of an ostomy appliance and the sealing between the ostomy appliance and the stoma.

If used with a one-piece ostomy appliance, such a sealing member would be difficult to manipulate for several reasons.

Firstly, it is very difficult to adapt the sealing member to the stoma after applying the ostomy appliance if the sealing member has a tacky surface on the side facing the bag as it will then adhere to the bag during attempts to adapt the sealing member to the stoma which must be performed by pressing the wall of the bag against the sealing member. Then, also a risk exists that the wall of the bag is torn when trying to disengage the contact.

Secondly, due to the measures to secure discretion, for decorative purposes and for providing softness, low noise generation and comfort stated above it also in this case very difficult, if not impossible for the user or the nurse to observe the stoma area during adaptation of such a sealing member when applying one-piece appliances.

SUMMARY OF THE INVENTION

The invention relates to an ostomy appliance comprising a front wall and a rear wall of flexible material forming a bag, said rear wall having an opening for receiving a stoma, and being provided with an adhesive wafer for securing the appliance to a user's skin, said wafer having a hole being aligned with the opening for receiving the stoma, wherein the opening of the rear wall has an edge being adapted to be secured to a surface of the adhesive wafer facing away from the user in an attachment zone surrounding the hole of the wafer, and wherein a first part of the edge of the opening of the rear wall is permanently secured to the surface of the wafer in a corresponding first part of the attachment zone, and a second, remaining part of the edge of the opening of the bag is prepared for adhesive sealing of the same to the remaining second part of the attachment zone.

Furthermore, the invention relates to a method of applying to the abdomen an ostomy appliance comprising a front wall and a rear wall of flexible material forming a bag, said rear wall having an opening for receiving a stoma, and said rear wall also being provided with an adhesive wafer for securing the appliance to a user's skin, said wafer having a hole being aligned with the opening for receiving the stoma, wherein the opening has an edge being secured to the surface of the adhesive wafer facing away from the user in an attachment zone surrounding the hole of the wafer.

Still further, the invention relates to a method of applying an ostomy appliance comprising a front wall and a rear wall of flexible material forming a bag, said rear wall having an opening for receiving a stoma, and said rear wall also being provided with an adhesive wafer for securing the appliance to a user's skin, said wafer having a hole being aligned with the opening for receiving the stoma, said hole comprising a sealing member having a second hole for receiving a stoma, wherein the opening has an edge being secured to the surface of the adhesive wafer facing away from the user in an attachment zone surrounding the hole of the wafer.

BRIEF DESCRIPTION OF THE DRAWINGS

The invention is disclosed more in detail with reference to the drawings in which FIG. 4 shows a stiffening element for use in an ostomy appliance of the invention.

FIG. 5a illustrates a notch in the stiffening element of FIG. 4.

FIG. 5b illustrates the notch with the stiffening element of FIG. 4 in a bent position.

DETAILED DESCRIPTION OF THE PRESENT INVENTION

Figure 1:
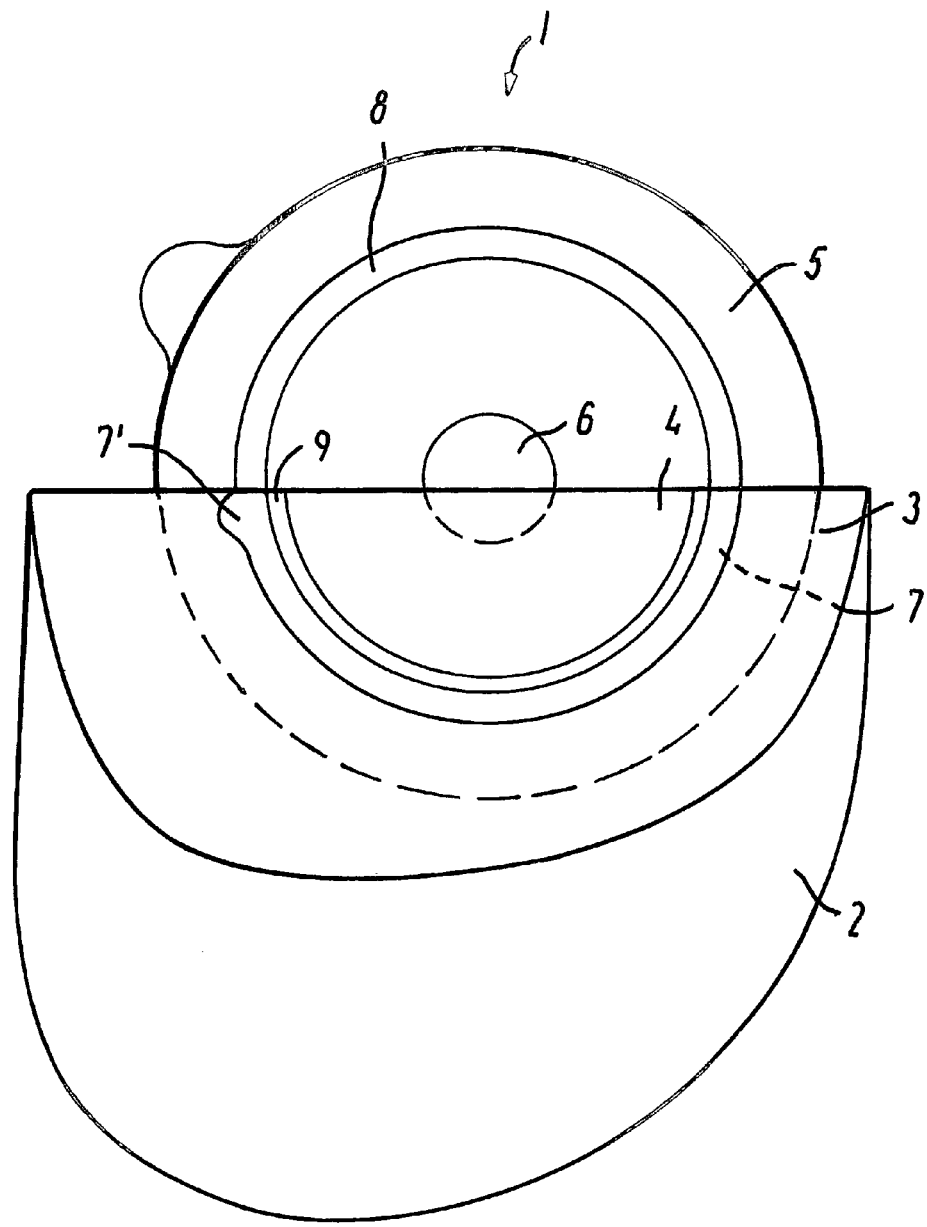
FIG. 1 shows an ostomy appliance of the invention in its open state.

According to a FIRST ASPECT the present invention relates to an ostomy appliance comprising a front wall and a rear wall of flexible material forming a bag, said rear wall having an opening for receiving a stoma, and being provided with an adhesive wafer for securing the appliance to a user's skin, said wafer having a hole being aligned with the opening for receiving the stoma, wherein the opening of the rear wall has an edge being adapted to be secured to a surface of the adhesive wafer facing away from the user in an attachment zone surrounding the hole of the wafer, and wherein a first part of the edge of the opening of the rear wall is permanently secured to the surface of the wafer in a corresponding first part of the attachment zone, and a second, remaining part of the edge of the opening of the bag is prepared for adhesive sealing of the same to the remaining second part of the attachment zone.

As a part of the edge of the bag of a one-piece appliance is not secured to the adhesive wafer, that part of the edge may be folded back giving access to the stoma area from the distal side of the appliance facing away from the user during the application of the appliance. Thus, a simple evaluation of the stoma area for cutting the wafer for adapting the same to the specific stoma and manipulation and location of an adhesive wafer in relation to the stoma is enabled. All such adaptation and application may be carried out having full view over the stoma area from the distal side. Then, the edge of the bag is easily sealed to the wafer along the remaining part of the attachment zone, and thus along the full periphery of the bag, using an adhesive. The adhesive is preferably protected by a release liner until the final sealing of the bag. The bag is preferably sealed permanently to the wafer. Thus, in use, after application the product works like a conventional one-piece appliance, and advantages of access to the stoma area when working with two-piece appliances are transferred to the one-piece technology.

The opening of the rear wall has an edge which is adapted to be secured to a surface of the adhesive wafer. Such securing may be achieved by attachment of the edge e.g. by means of an adhesive. In some embodiments only the edge of the rear wall is adapted to be secured to the surface of the adhesive wafer while in other embodiments also an area adjacent to the edge may be secured or attached to the surface of the adhesive wafer.

A release liner may be provided on the second remaining part of the edge of the opening of the rear wall. In order to adhere the second remaining part of the rear wall to the wafer the release liner must be removed.

In one embodiment the second, remaining part of the edge of the opening of the rear wall is adapted to be changed from a first position wherein is in not adhesively sealed to the remaining second part of the attachment zone, and a second position wherein it is adhesively sealed to the remaining second part of the attachment zone.

In an embodiment the second, remaining part of the edge of the opening of the bag is prepared for permanently adhesive sealing of the same to the remaining second part of the attachment zone. Thus in the latter embodiment when the second remaining part has been permanently adhered to the second part of the attachment zone it may be difficult or even impossible to remove it again. Accordingly if one succeeds in removing the second part it can not be re-attached again.

The resulting hole may however show an exposed edge which does not provide a sufficient sealing against a stoma ensuring that no leak occurs and may injure the surface of the stoma e.g. when the user bends or turns due to the exposed edge of the carrier sheet which after cutting even may show a serrated edge.

In one embodiment the ostomy appliance is in the form of a set which comprises a separate sealing member for disposing in the hole of the wafer surrounding the stoma and having a hole for accommodating the stoma. The present invention enables the use of such a sealing member together with one-piece ostomy appliances and enables an easy manipulation and shaping of such sealing member before application and to seal between the adhesive wafer and the stoma avoiding direct contact between the stoma and the edge of the hole. Thus, the edge of the hole of the sealing member may be everted or rolled and the sealing member positioned from the distal side of the appliance or from "inside the bag".

The use of a separate sealing member also enables a reduction in the number of available sizes of holes as one or a few large sizes of holes may be tailored to most stomas using the separate sealing member, which has not been possible for one-piece ostomy appliances until now. Furthermore, the cutting for enlarging the hole of a one-piece ostomy appliance for accommodating a stoma is rendered easier as the fit is not critical.

In accordance with a suitable embodiment of the invention, the second part of the edge of the bag is secured to one surface of a stiffening element reducing the risk of wrinkling of the edge of the bag.

When the first and the second part of the edge of the bag are secured to a first and a second part, respectively, of one surface of the stiffening element, the handling of the bag and the securing of the first part of the edge of the bag to the first part of the attachment zone are facilitated and the process is readily adapted for automatic production.

A stiffening element is preferably in the form of a ring being secured to the circumference of the opening of the bag. Such stiffening element may suitably be made from a plastics material, which is flexible and relatively rigid so that it is substantially dimensionally stable under normally occurring loads. Polyolefins, particularly polyethylene, e.g. in the form of a blend of high and low density polyethylenes, have been found suitable, but other materials having similar properties may be used. The stiffening element may alternatively be in the form of a flange of a foam material such as a cellular plastic material conventionally used for production of flanges for ostomy appliances. A polyurethane foam is suitably used.

The adhesive for adhesive sealing of the second part of the edge of the bag and the stiffening element to the second part of the attachment zone is suitably an "aggressive" adhesive material providing an immediate grip when contacted with the other surface after removing a release liner. It is preferred that the adhesive material has a sufficient thickness and is sufficiently mouldable to provide a reliable sealing of the edge of the bag. A suitable adhesive material is pressure sensitive adhesive suitable for use with the parts to be united such as acrylic adhesives, elastomeric adhesives, polyurethane adhesives, or polyester adhesives. The choice of adhesive may be made in accordance with the above requirements, as it is not critical for the invention in the respect that the adhesive is not in contact with the skin. It is also contemplated that the adhesive properties of the adhesive and the second part of the edge of the bag or the stiffening element and the second part of the attachment zone are balanced enabling an opening and resealing of the bag, if desired.

It is suitable when the stiffening element is a flat ring provided with two notches dividing the flat ring into two parts. The shape of such ring should correspond to the shape of the attachment zone and may e.g. be circular or elliptical. Such notches provide predetermined zones in which the stiffening element is readily folded back giving access to the distal side of the adhesive wafer. The notches may be present on the proximal surface of the stiffening element of on the distal surface of the stiffening element whichever deemed most appropriate. When placed on the distal surface of the stiffening element, care must be taken when securing the edge of the bag to the stiffening element that the edge of the bag is reliably sealed to the surface without canals in the notch-area. The securing may e.g. be effected by welding or suitably applying an adhesive, preferably in an amount ensuring a reliable sealing in the notch-area. A combination of a welding seam and adhesive sealing may be used if deemed appropriate.

It is especially suitable to locate the notches stretch essentially along a chord of the circular ring facilitating the bending of the stiffening element. The notches stretch essentially along a diameter of the circular ring giving a large opening to the stoma site in the ostomy appliance.

In one embodiment of the invention the part of the stiffening element secured the second part of the bag is provided with an adhesive layer being covered by a protecting layer. In case that the notches are located on the proximal surface of the stiffening element, care must be taken to ensure that the notch is sealed reliably when adhering the second of the edge of the bag to the second part of the attachment zone, e.g. by applying a sufficient amount of adhesive material to fill the notch.

A stiffening element to be used in accordance with the present invention may be made by a method known per se for manufacturing products from the selected materials such as injection moulding, die casting, pressing, or foaming using corresponding moulds. Alternatively, a stiffening element may be cut from a work-piece of the desired material such as a foam block. A notch may be prepared when forming the stiffening element or later using methods known per se such as cutting or milling.

In another embodiment of the invention the second part of the attachment zone of the wafer is provided with an adhesive layer being covered by a protecting layer. In case that the notches are located on the proximal surface of the stiffening element, care must also be taken in this case to ensure that the notch is sealed reliably when adhering the second of the edge of the bag to the second part of the attachment zone, e.g. by applying a sufficient amount of adhesive material at the site of the attachment zone near the notch to fill the notch.

In a further embodiment of the invention, the front wall is provided with an opening provided with cover, which may be released and resealed and thus giving temporary access to the internal space of the bag for inspection of the stoma area during the service time of the ostomy appliance. Such opening is especially of interest in the first period after a stoma having been made in order to allow an inspection of the newly formed stoma without having to remove the appliance and also for establishing a suitable regime for exchange of appliances for the ostomate in question. The opening may be provided with a closure corresponding to an adhesive coupling normally used for coupling of collection bags to ostomy body side members of two-piece appliances or a conventional coupling ring for coupling of collection bags to ostomy body side members of two-piece appliances and a matching closure such as the closure disclosed in WO 98/38952.

In a SECOND ASPECT the invention relates to a method of applying an ostomy appliance comprising a front wall and a rear wall of flexible material forming a bag, said rear wall having an opening for receiving a stoma, and being provided with an adhesive wafer for securing the appliance to a user's skin, said wafer having a hole being aligned with the opening for receiving the stoma, wherein the opening of the rear wall has an edge being adapted to be secured to a surface of the adhesive wafer facing away from the user in an attachment zone surrounding the hole of the wafer, and wherein a first part of the edge of the opening of the rear wall is permanently secured to the surface of the wafer in a corresponding first part of the attachment zone, and a second, remaining part of the edge of the opening of the bag is prepared for adhesive sealing of the same to the remaining second part of the attachment zone, said method comprising locating the stoma, adapting the size of the hole of the adhesive wafer to the stoma, aligning the stoma and the hole of the adhesive wafer, placing the adhesive wafer on the abdomen of the ostomate with the stoma projecting into the hole of the wafer and sealing the bag by bringing the remaining part of the edge of the bag into adhesive contact with the remaining second part of the attachment zone.

Alternatively the second aspect could relate to a method of applying an ostomy appliance comprising a front wall and a rear wall of flexible material forming a bag, said rear wall having an opening for receiving a stoma, and said rear wall also being provided with an adhesive wafer for securing the appliance to a user's skin, said wafer having a hole being aligned with the opening for receiving the stoma, wherein the opening has an edge being secured to the surface of the adhesive wafer facing away from the user in an attachment zone surrounding the hole of the wafer, wherein a first part of the edge of the opening of the bag is secured to the surface of the wafer in a corresponding first part of the attachment zone, and wherein a second, remaining part of the edge of the opening of the bag is prepared for adhesive sealing of the same to the remaining second part of the attachment zone, said method comprising locating the stoma, adapting the size of the hole of the adhesive wafer to the stoma, aligning the stoma and the hole of the adhesive wafer, placing the adhesive wafer on the abdomen of the ostomate with the stoma projecting into the hole of the wafer and sealing the bag by bringing the remaining part of the edge of the bag into adhesive contact with the remaining second part of the attachment zone.

The ostomy appliance according to the second aspect of the present invention may comprise any feature and/or element of the ostomy appliance of the first aspect of the present invention.

In a THIRD ASPECT the invention relates to a method of applying an ostomy appliance comprising a front wall and a rear wall of flexible material forming a bag, said rear wall having an opening for receiving a stoma, and being provided with an adhesive wafer for securing the appliance to a user's skin, said wafer having a hole being aligned with the opening for receiving the stoma, wherein the opening of the rear wall has an edge being adapted to be secured to a surface of the adhesive wafer facing away from the user in an attachment zone surrounding the hole of the wafer, and wherein a first part of the edge of the opening of the rear wall is permanently secured to the surface of the wafer in a corresponding first part of the attachment zone, and a second, remaining part of the edge of the opening of the bag is prepared for adhesive sealing of the same to the remaining second part of the attachment zone, said method comprising locating the stoma, aligning the stoma and the hole of the adhesive wafer, placing the adhesive wafer on the abdomen of the ostomate with the stoma projecting into the hole of the wafer, locating the sealing member, enlarging the second hole of the sealing member by everting or rolling an inner rim of the second hole adapting the size and shape of the hole to the stoma, aligning the stoma and the second hole, placing the sealing member on the abdomen of the ostomate with the stoma projecting into the second hole, and bringing the sealing member to seal between the adhesive wafer and the stoma.

Alternatively the third aspect could relate to a method of applying an ostomy appliance comprising a front wall and a rear wall of flexible material forming a bag, said rear wall having an opening for receiving a stoma, and said rear wall also being provided with an adhesive wafer for securing the appliance to a user's skin, said wafer having a hole being aligned with the opening for receiving the stoma, said hole comprising a sealing member having a second hole for receiving the stoma, wherein the opening has an edge being secured to the surface of the adhesive wafer facing away from the user in an attachment zone surrounding the hole of the wafer, wherein a first part of the edge of the opening of the bag is secured to the surface of the wafer in a corresponding first part of the attachment zone, and wherein a second, remaining part of the edge of the opening of the bag is prepared for adhesive sealing of the same to the remaining second part of the attachment zone, said method comprising locating the stoma, aligning the stoma and the hole of the adhesive wafer, placing the adhesive wafer on the abdomen of the ostomate with the stoma projecting into the hole of the wafer, locating the sealing member, enlarging the second hole of the sealing member by everting or rolling an inner rim of the second hole adapting the size and shape of the hole to the stoma, aligning the stoma and the second hole and placing the sealing member on the abdomen of the ostomate with the stoma projecting into the second hole, and bringing the sealing member to seal between the adhesive wafer and the stoma.

The ostomy appliance according to the third aspect of the present invention may comprise any feature and/or element of the ostomy appliance of the first aspect of the present invention.

The adhesive wafer may comprise any skin-friendly adhesive known per se, e.g. an adhesive comprising hydrocolloids or other moisture absorbing constituents for prolonging the time of use forming the surface to be secured to the user's skin. The adhesive may e.g. be of the type disclosed in those disclosed in U.S. Pat. Nos. 4,367,732, 5,051,259, 5,714,225, 6,171,594, 6,303,700, 6,451,883, or 6,437,038, or in WO Publication Nos. 00/54820, or 01/05340.

A sealing member may suitably be made of a material of the kind disclosed in U.S. Pat. No. 6,509,391, or 6,332,879. Thus, the elastic and plastic properties may be selected by the skilled in the art in accordance with the desired properties for the actual purpose, including a self-sealing effect obtainable using a sealing member made from an adhesive material showing absorbing and swelling properties when contacted by aqueous material.

A carrier sheet may be present on the surface of the adhesive wafer facing the bag and may any suitable thermoplastic material known per se for use in the preparation of ostomy appliances e.g. a foam, a non-woven layer or a polyurethane, polyethylene, polyester or polyamide suitable for attachment of a collecting bag using an adhesive or by welding.

The collection bag may be made in analogy with and from materials conventionally used for the preparation of ostomy appliances. Such materials are suitably films composed of any suitable material, which is heat sealable and sufficiently impervious for unpleasant odours such as polyolefin films or combinations of such films, e.g. polyethylene or a coextrudate of polyethylene and polyvinylidene chloride. Suitably the bag is made from front and rear walls welded in a manner known per se along the rim forming a bag. When cutting or punching the walls, an opening for receiving a stoma is suitably also punched in the wall to form the rear wall.

A protective cover or release liner may for instance be siliconized paper. It does not need to have the same contour as the dressing, e.g. a number of dressings may be attached to a larger sheet of protective cover. The protective cover is not present during the use of the dressing of the invention and is therefore not an essential part of the invention.

DESCRIPTION OF THE PREFERRED EMBODIMENTS

Reference is made to FIG. 1 showing an ostomy appliance 1 of the invention in its open state. The ostomy appliance comprises a front wall 2 and a rear wall 3 of flexible material forming a bag, said rear wall having an opening 4 for receiving a stoma, and said rear wall also being provided with an adhesive wafer 5 for securing the appliance to a user's skin, said wafer having a hole 6 being aligned with the opening for receiving the stoma, wherein the opening has an edge 7,7' being secured to the surface of the adhesive wafer facing away from the user in an attachment zone 8 surrounding the hole of the wafer. The attachment zone 8 is formed as a single adhesive attachment ring around the hole of the wafer. A first part of the edge 7 of the bag is secured to the surface of the wafer in a corresponding first part of the attachment zone, and wherein a second, remaining part 7' of the edge of the bag is prepared for adhesive sealing of the same to the remaining second part 8 of the attachment zone. The edge of the opening of the bag is provided with a stiffening element 9.

Figure 2:
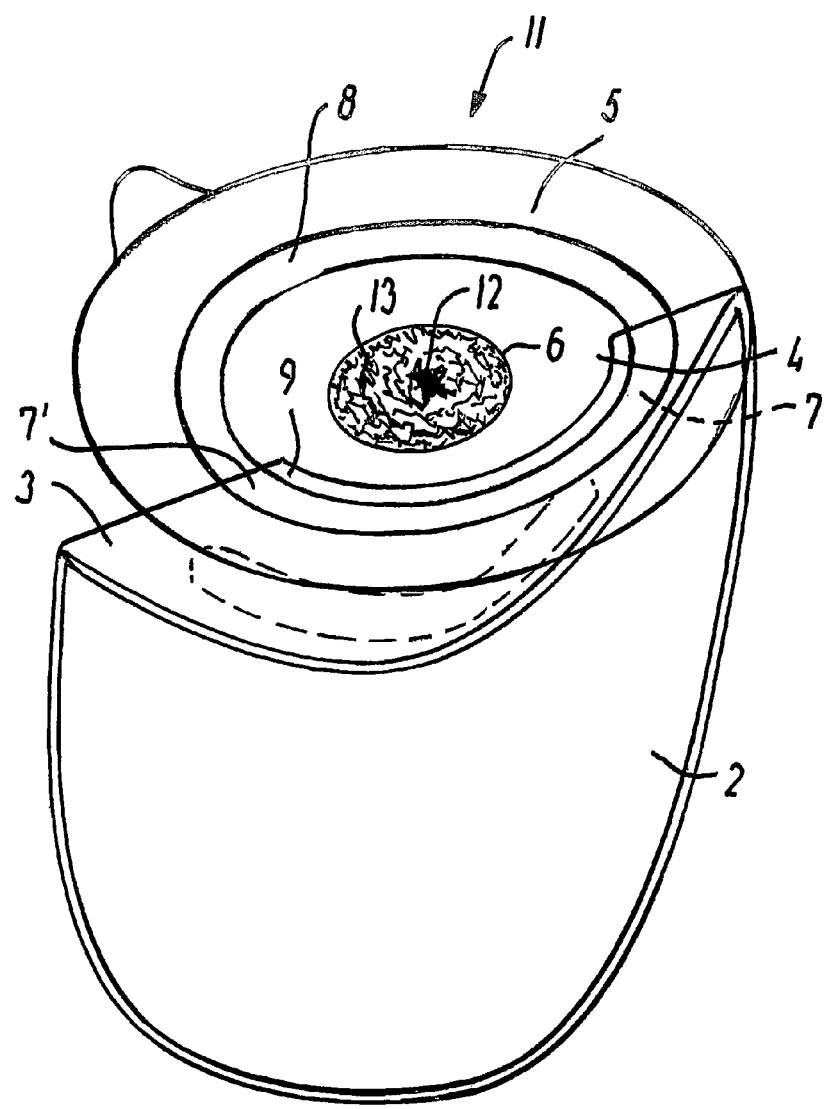
FIG. 2 shows another embodiment of an ostomy appliance of the invention in its open state applied to a users abdomen.

FIG. 2 shows another embodiment of an ostomy appliance 11 of the invention in its open state applied to a users abdomen. The ostomy appliance comprises a front wall 2 and a rear wall 3 of flexible material forming a bag, said rear wall having an opening 4 for receiving a stoma 12, and said rear wall also being provided with an adhesive wafer 5 for securing the appliance to a user's skin, said wafer having a hole 6 being aligned with the opening for receiving the stoma, wherein the opening has an edge 7,7' being secured to the surface of the adhesive wafer facing away from the user in an attachment zone 8 surrounding the hole of the wafer, wherein a first part of the edge 7 of the bag is secured to the surface of the wafer in a corresponding first part of the attachment zone, and wherein a second, remaining part 7' of the edge of the bag is prepared for adhesive sealing of the same to the remaining second part 8 of the attachment zone. The edge of the opening of the bag is provided with a stiffening element 9. In the hole 6 of the wafer is a separate sealing member 13 sealing against the stoma and the edge of the hole of the wafer.

Figure 3:
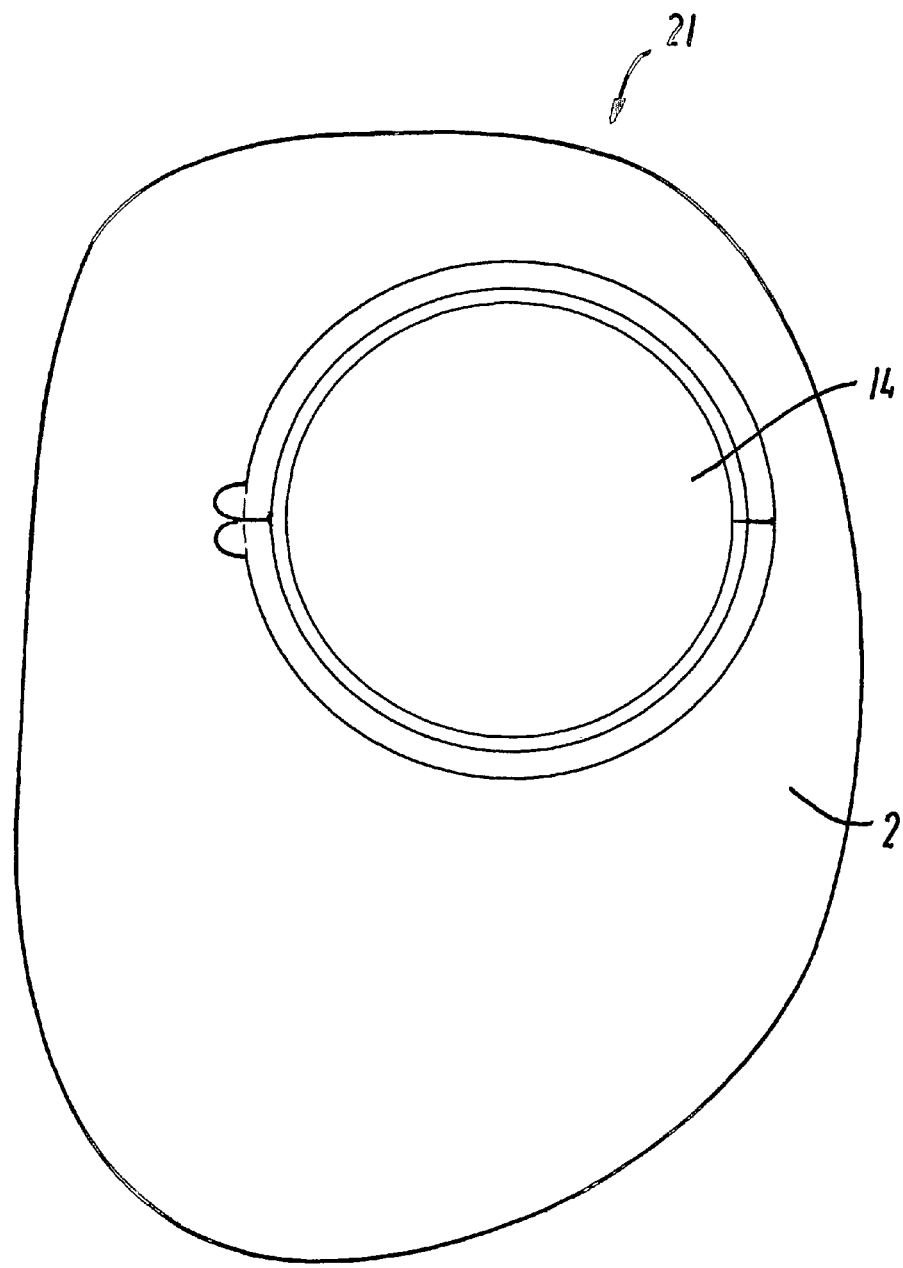
FIG. 3 shows further embodiment of an ostomy appliance of the invention in its closed state.

FIG. 3 shows further embodiment of an ostomy appliance 21 of the invention in its closed state seen from the surface facing away from the user. The ostomy appliance corresponds to the embodiment shown in FIG. 1 except that in front wall 2 is provided with an opening provided with cover 14, which may be released and resealed and thus giving temporary access to the internal space of the bag for inspection of the stoma area during the service time of the ostomy appliance.

FIGS. 4, 5a and 5b show a stiffening element 31 for use in an ostomy appliance of the invention. The stiffening element is in the form of a circular ring 32 provided with two notches 33 dividing the circular ring into two parts—a first part 34 and a second part 36. The notches provide predetermined zones in which the stiffening element is readily folded. The notches are in this embodiment placed on the surface to be attached to an adhesive wafer of an ostomy appliance of the invention.

The invention claimed is:

1. A one-piece ostomy appliance comprising:
    a single bag, the single bag is a body waste collection bag having a front wall and a rear wall;
    an opening formed in the rear wall of the single bag and configured to receive a stoma;
    an adhesive wafer having a hole alignable with the opening formed in the rear wall of the single bag, a first side of the wafer having a skin securing adhesive layer and a second side of the wafer positioned to abut the rear wall of the single bag, the second side of the wafer including a single adhesive attachment ring surrounding the hole; and
    a first edge of the opening formed in the rear wall of the single bag is permanently secured to the single adhesive attachment ring and a remaining second edge of the opening formed in the rear wall of the single bag is adhesively attached to the single adhesive attachment ring, the remaining second edge of the opening formed in the rear wall of the single bag is removable from and resealable to the single adhesive attachment ring and so configured to allow the remaining second edge of the opening formed in the rear wall of the single bag to be removed from the single adhesive attachment ring for accessing and for viewing of the stoma.

2. The ostomy appliance as claimed in claim 1, further comprising a stiffening element disposed on the rear wall of the single bag and positioned to abut the single adhesive attachment ring.

3. The ostomy appliance as claimed in claim 1, further comprising a stiffening element disposed on the rear wall of the single bag and positioned to abut both the first edge and the remaining second edge of the opening formed in the rear wall of the single bag to the single adhesive attachment ring.

4. The ostomy appliance as claimed in claim 1 wherein the single adhesive attachment ring is attached to a stiffening element.

5. The ostomy appliance as claimed in claim 1, further comprising:
    a removable release liner positioned on the remaining second edge of the opening formed in the rear wall of the single bag.

6. A one-piece ostomy appliance comprising:
    a single bag that is a body waste collection bag having a front wall and a rear wall;
    an opening disposed in the rear wall of the body waste collection bag and configured to receive a stoma;
    an adhesive wafer having a hole alignable with the opening, a first side of the wafer having a skin securing adhesive layer and a second side of the wafer positioned to abut the rear wall of the body waste collection bag, the second side of the wafer including a single adhesive attachment ring surrounding the hole;
    wherein the body waste collection bag has an attachment zone that includes a first part and a second part, the first part of the attachment zone of the body waste collection bag is permanently secured to the single adhesive attachment ring and the second part of the attachment zone of the body waste collection bag is removably attachable to and detachable from the single adhesive attachment ring of the adhesive wafer.

7. The ostomy appliance as claimed in claim 6, further comprising a stiffening element disposed around the opening disposed on the rear wall of the body waste collection bag and positioned to abut the single adhesive attachment ring.

8. The ostomy appliance as claimed in claim 6, further comprising a stiffening element disposed around the single adhesive attachment ring.

9. The ostomy appliance as claimed in claim 6, further comprising a removable release liner positioned on the second part of the attachment zone of the body waste collection bag.

* * * * *